United States Patent
Kanikanti et al.

[11] Patent Number: 5,900,425
[45] Date of Patent: May 4, 1999

[54] PHARMACEUTICAL PREPARATIONS HAVING CONTROLLED RELEASE OF ACTIVE COMPOUND AND PROCESSES FOR THEIR PREPARATION

[75] Inventors: Venkata-Rangarao Kanikanti, Leverkusen; Wolfgang Mück, Wuppertal; Andreas Ohm, Neuss; Peter Kurka, Langenfeld; Gerd Toppel, Odenthal, all of Germany

[73] Assignee: Bayer Aktiengesellschaft, Leverkusen, Germany

[21] Appl. No.: 08/934,308

[22] Filed: Sep. 19, 1997

Related U.S. Application Data

[63] Continuation of application No. 08/637,892, Apr. 25, 1996, abandoned.

[30] Foreign Application Priority Data

May 2, 1995 [DE] Germany .............................. 195 15 972

[51] Int. Cl.⁶ ................................ A61K 9/14; A61K 9/20; A61K 31/44
[52] U.S. Cl. ........................... 514/356; 514/772; 514/781; 514/784; 514/788; 514/965; 424/457; 424/461; 424/462; 424/463; 424/464; 424/465; 424/468; 424/469; 424/470

[58] Field of Search ...................................... 514/356, 772, 514/781, 784, 788, 965; 424/457, 461, 462, 463, 464, 465, 468, 469, 470

[56] References Cited

U.S. PATENT DOCUMENTS

| Re. 33,963 | 6/1992 | Hegasy | 424/78.24 |
|---|---|---|---|
| 4,412,986 | 11/1983 | Kawata et al. | 424/80 |
| 4,801,460 | 1/1989 | Goertz et al. | 424/465 |
| 4,880,585 | 11/1989 | Klimesch et al. | 264/141 |
| 4,892,730 | 1/1990 | Hegasy | 424/80 |
| 4,981,683 | 1/1991 | Hegasy | 424/80 |
| 5,015,479 | 5/1991 | Mulligan et al. | 424/457 |
| 5,128,142 | 7/1992 | Mulligan et al. | 424/457 |

FOREIGN PATENT DOCUMENTS

| 078430 | 5/1983 | European Pat. Off. |
|---|---|---|
| 219161 | 4/1987 | European Pat. Off. |
| 274176 | 7/1988 | European Pat. Off. |
| 0429187 | 5/1991 | European Pat. Off. |
| 552708 | 7/1993 | European Pat. Off. |

*Primary Examiner*—Frederick Krass
*Attorney, Agent, or Firm*—Sprung Kramer Schaefer & Briscoe

[57] ABSTRACT

The invention relates to pharmaceutical preparations having controlled release of active compound and to processes for their preparation, in particular for poorly soluble active compounds having problematic bioavailability.

4 Claims, No Drawings

PHARMACEUTICAL PREPARATIONS HAVING CONTROLLED RELEASE OF ACTIVE COMPOUND AND PROCESSES FOR THEIR PREPARATION

This application is a continuation, of application Ser. No. 08/637,892, filed on Apr. 25, 1996 which is abandoned.

The invention relates to pharmaceutical preparations having controlled release of active compound and to processes for their preparation, in particular for poorly soluble active compounds having problematic bioavailability.

Numerous pharmaceutical active compounds having low water solubility can only be formulated with difficulty into pharmaceutical formulations which are sufficiently stable on storage and have an adequate bioavailability. To achieve adequate bioavailability, poorly soluble active compounds, e.g. dihydropyridines, are supplied as preparations which exhibit high release rates within a short time in order to obtain adequate plasma levels.

It is known that active compounds in amorphous or dissolved form often have a higher bioavailability than the corresponding crystalline active compounds. In particular, compounds having a tendency to recrystallize cause problems, as often their bioavailability is not reproducible or decreases significantly after relatively long storage times.

To improve safety and patient compliance, it is desirable, in particular for long-term treatments, to reduce the daily administration frequency, e.g. to once or twice daily.

The invention relates to an orally administrable solid, stable pharmaceutical preparation having high bioavailability and controlled, long-lasting release, comprising 1 part by weight of the active compound in amorphous form as a coprecipitate in 0.5 to 10 parts by weight of polyvinylpyrrolidone, preferably 1.0 to 5.0 parts by weight, having an average molecular weight of about 15,000 to 1,000,000, preferably up to 100,000, and a release-delaying component consisting essentially of 0.01 to 15.0 parts by weight of a gel-forming polymer and, if appropriate, other auxiliaries and fillers.

This unexpected improvement in the storage stability of active compound coprecipitates and controlled release pharmaceutical preparations comprising the latter was found as a general principle for poorly water-soluble active compounds.

Examples which may be mentioned are the dihydropyridines, such as nifedipine, nimodipine, nitrendipine, nisoldipine, felodipine or nicardipine, non-steroidal anti-inflammatory active compounds such as ketoprofen, ibuprofen or flurbiprofen or antibacterial active compounds, e.g. from the suphonamide, quinolone, tetracycline or macrolide classes. Particularly typical representatives which may be mentioned are the active compounds nimodipine and nifedipine. Nimodipine and nifedipine have a solubility of only about 1.0 and 7.0 mg/l. The nimodipine tablets on the market until now exhibit a rapid release of active compound and require administration three times daily in order to guarantee adequate plasma levels (DE 32 05 399). The nimodipine controlled-release tablets according to the invention exhibit a long-lasting action and require administration twice daily.

Previous attempts to prepare a nimodipine delayed-release formulation on the basis of conventional technologies, e.g. using very finely ground nimodipine crystals, did not lead to success. All attempts with this poorly soluble active compound resulted in too low a bioavailability.

The known method of dissolving active compounds in amorphous form in polymers which are liquefied by heating (melt process or melt extrusion process) is very complicated and needs a relatively large proportion of auxiliary (compare EP 0 240 904 and EP-A-0 240 906) excipients.

Another method of increasing the release rate of poorly soluble active compounds is adsorption of the active compounds together with a pharmacologically inactive pharmaceutical auxiliary on a crosslinked polymer. An essential component of all these adsorbates is the water-insoluble, crosslinked polymer. These adsorbates are mixed with swellable polymers to prepare controlled-release formulations (EP 0 429 187 and U.S. Pat. No. 5,128,142).

Surprisingly, it has been found that delayed-release tablets containing poorly-soluble active compounds can be prepared even without the crosslinked polymers. The proportion of auxiliary materials in the tablet is thus distinctly reduced and a smaller, easier-to-swallow tablet can be prepared.

It also appears that the controlled-release tablets prepared in this way exhibit a surprisingly high storage stability. When in-vitro tests are carried out, they exhibit an almost linear release and crystalline active compound is no longer detectable by customary methods, e.g. X-ray analysis, in the respective coprecipitates or dosage forms.

The controlled-release preparations according to the invention can have a customary composition of active compounds and auxiliaries. They preferably contain 1 part by weight of active compound in amorphous form, 0.5 to 10 parts by weight, preferably 1 to 4 parts by weight, of the coprecipitate-forming polymer, in particular polyvinylpyrrolidone (PVP) having an average molecular weight of 15,000 to 1,000,000 and optionally 0.01 to 15.0 parts by weight, preferably 0.1 to 4 parts by weight, of a gel former, preferably hydroxypropylmethylcellulose (HPMC). Further processing to give a controlled-release form is likewise carried out by customary methods, e.g. if necessary by the additional use of one or more polymers which form gels in the presence of water. The total amount of the gel-forming polymers needed is dependent on the retardation effect desired and can be varied appropriately in a customary manner.

In the case of the active compound-polymer coprecipitate, organic solvents are preferably employed which simultaneously dissolve the active compound and the polymer. Active compounds and polymers can also be dissolved separately in different solvents and the solutions then mixed. Particularly suitable solvents are the low molecular weight halogenated hydrocarbons, ketones and/or alcohols each having up to 6 C atoms, in particular having up to 4 C atoms. Of particular interest are solvents which can be removed and recovered again in a simple manner, such as acetone, methylene chloride, chloroform, ethanol, methanol and isopropanol or their mixtures.

Suitable coprecipitate formers are the customary polymers, in particular PVP having an average molecular weight of 15,000 to 1,000,000, preferably the PVP types on the market, including their copolymers, which are marketed under the names KOLLIDON 12PF, –17PF, –25, –30, –90 or -VA64.

Suitable gel formers are also the customary polymers, preferably the cellulose ethers having low, average or high viscosity such as hydroxymethylcellulose, hydroxyethylcellulose, hydroxypropylcellulose, hydroxybutylcellulose, hydroxypropylmethylcellulose, sodium carboxymethyl cellulose, calcium carboxymethylcellulose, methylcellulose, ethylcellulose and/or polyethylene glycols. Cellulose ethers can be employed as release-delaying components and also as coprecipitate formers.

One possibility for the preparation of the coprecipitates is the dissolution of one part by weight of the active compound with 0.5 to 10 parts by weight, preferably 1 to 4 parts by weight, of the coprecipitate-forming polymer (PVP) and optionally the cellulose ether in an amount of organic solvent in which both components dissolve or separate solutions of active compound and polymer in different solvents and combination of these solutions to give one solution. This solution can be used directly for granulating the 0.01 to 13 parts by weight, preferably 0.1 to 2 parts by weight, of gel former and/or other auxiliaries or alternatively the other auxiliaries/gel formers can be suspended in this solution and the organic solvent can then be removed. The removal of the solvent is carried out by customary methods, e.g. at elevated temperatures between 70 and 150° C., preferably between 90 and 120° C., under a pressure of 5 to 200 mbar. Customary spray-drying processes are also suitable for this purpose. If necessary, this drying can take place under a nitrogen atmosphere. The duration of the drying is determined by the nature and amount of the solvent and the other components and can be between 30 minutes and 3 days. Drying preferably takes place within 2 to 48 hours. The dry coprecipitate obtained. can optionally be subjected additionally to a dry compaction step in order to achieve, for example, a desired bulk volume of about 1.5 to 3.5 ml/g.

The coprecipitate premixture thus obtained can be converted into finished pharmaceutical preparations either directly or by addition of an additional release-delaying component or auxiliaries. When preparing controlled-release preparations, this is carried out, for example, by mixing 1 part by weight of premixture with up to 10 parts by weight of a gel-forming polymer and, if appropriate, further auxiliaries. Additional gel formers are only employed if required, i.e. the total amount of gel former controls the release rate. This mixture is then further processed by customary methods to give tablets or other solid dosage forms.

Gel-forming polymers of the release-delaying components which may be mentioned are preferably hydroxyethylcellulose (HEC), hydroxypropylcellulose (HPC), hydroxypropylmethylcellulose (HPMC), sodium carboxymethylcellulose (Na CMC), methylcellulose (MC) and ethylcellulose (EC). Particularly suitable cellulose derivatives are those based on HPMC. Other gel formers such as sodium alginate, carrageenans, galactomannan, agar-agar, gum arabic, guar gum, xanthan gum and carboxypolymethylene or derivatives of starches, pectins, chitin, polyethylene glycol, polyvinyl alcohol, copolymers of acrylic and methacrylic acid esters and their mixtures can also be employed. Preferably those polymers are used which have a viscosity of a 2% w/w solution at 20° C. of at least 15 mPa.s.

The controlled-release preparations according to the invention expediently contain 10 to 400 mg of active compound per individual preparation. In the case of controlled-release preparations, the dose is 20 to 400 mg, preferably 30 to 120 mg of active compound per individual dose.

The controlled-release preparations according to the invention produce positive effects especially if the residual solvent content in the coprecipitate is not too high. Preferably, the residual solvent content should be not greater than 1% by weight, based on the weight of the coprecipitate, preferably less than 0.8% by weight.

The controlled-release coprecipitate tablets according to the invention, which contain, for example, 90 mg of amorphous nimodipine, exhibit extremely good storage stability. With knowledge of the prior art, it was not to be expected that a stable and small delayed-release coprecipitate tablet having satisfactory bioavailability for poorly soluble active compounds such as nimodipine or nifedipine can be prepared without water-insoluble crosslinked polymers (see EP 0 429 187 and U.S. Pat. No. 5 128 142).

In the case of light-sensitive active compounds such as nifedipine and nimodipine, the controlled-release tablets must then be provided with a light-protective coating in order that the active compound is not degraded by the light. The coating is carried out, for example, by spraying an aqueous suspension consisting of: HMPC (film former), PEG (plasticizer), titanium dioxide and iron oxide (light-scattering and absorbing pigments). During the coating procedure, hot air is blown onto the tablet bed.

The following working examples illustrate the subject of the invention without restricting it.

Preparation of active compound-coprecipitate/intermediate

EXAMPLE 1

1 kg of nimodipine is dissolved together with 2.5 kg of PVP (MW 29,000) in sufficient acetone. The acetone is then removed at elevated temperature and reduced pressure down to a residual solvent content of less than 0.6%. The dried coprecipitate is screened and the fine powder obtained can be further processed by customary methods to give tablets.

EXAMPLE 2

In analogy to Example 1, a coprecipitate containing 1 part of nimodipine and 2.5 parts of PVP and 1 part of HPMC 50 CP is prepared. Instead of acetone the solvent isopropanol is employed.

EXAMPLE 3

In analogy to Example 2, instead of HPMC 50 CP the polymer HPMC 1500 CP is employed.

EXAMPLE 4

In analogy to Example 2, instead of HPMC 50 CP the polymer HPMC 4000 CP is employed.

EXAMPLE 5

In analogy to Example 1, 2.5 kg of PVP of average molecular weight 45,000 are employed.

EXAMPLE 6

In analogy to Example 2, 1.5 kg of PVP of molecular weight 1,000,000 are employed and also, instead of isopropanol, the solvent ethanol is employed. The ethanolic solution of nimodipine and PVP is clear before HPMC 50 CP is added.

EXAMPLE 7

Composition is as in Example 4. Nimodipine and PVP are dissolved in acetone or nimodipine is separately dissolved in acetone and PVP in ethanol and the solutions are then mixed. This clear solution is used for granulation with HPMC 4000 CP. The solvent is then removed by customary methods.

EXAMPLE 8

In analogy to Example 7, instead of nimodipine the active compound nifedipine is employed.

EXAMPLE 9

In analogy to Example 8, 1.5 kg of PVP of molecular weight 1,000,000 are employed.

EXAMPLE 10

In analogy to Example 8, instead of HMPC 4,000 CP the polymer HPMC 100,000 CP is employed. 3.0 kg of PVP (MW 29,000) are employed.

EXAMPLE 11

In analogy to Example 8, instead of PVP the copolymer Copolyvidon/Kollidon VA 64 is employed.

EXAMPLE 12

In analogy to Example 1, instead of acetone the solvent ethanol is employed and instead of PVP the polymer HPMC 15,000 CP is employed.

EXAMPLE 13

In analogy to Example 1, instead of acetone the solvent isopropanol is employed.

EXAMPLE 14

In analogy to Example 1, instead of acetone the solvent methylene chloride is employed.

EXAMPLE 15

The coprecipitate which was obtained analogous to Example 7 is prepared under reduced pressure (<300 mbar) in a fluidized-bed granulator by spray granulation at temperatures between 60 and 120° C.

EXAMPLE 16

In analogy to Example 1, instead of nimodipine the active compound nifedipine and 2.0 kg of PVP (MW 29,000) are employed.

EXAMPLE 17

In analogy to Example 1, instead of nimodipine the active compound ketoprofen is employed.

EXAMPLE 18

In analogy to Example 1, 1.5 kg of PVP of average molecular weight 1,000,000 are employed. Instead of acetone ethanol is employed.

EXAMPLE 19

In analogy to Example 12, instead of HPMC the polymer hydroxypropylcellulose (HPC) is employed.

EXAMPLE 20

In analogy to Example 19, instead of HPC the polymer methylcellulose (MC) is employed.

EXAMPLE 21

In analogy to Example 20, instead of MC the polymer hydroxyethylcellulose (HEC) is employed).

EXAMPLE 22

In analogy to Example 18, instead of nimodipine the active compound nifedipine is employed.

EXAMPLE 23

In analogy to Example 5, instead of nimodipine the active compound nifedipine is employed.

EXAMPLE 24

In analogy to Example 12, instead of nimodipine the active compound nifedipine is employed.

EXAMPLE 25

In analogy to Example 19, instead of nimodipine the active compound nifedipine is employed.

EXAMPLE 26

In analogy to Example 20, instead of nimodipine the active compound nifedipine is employed.

EXAMPLE 27

In analogy to Example 21, instead of nimodipine the active compound nifedipine is employed.
Introduction and/or potentiation of the release-delaying component and further processing as a solid pharmaceutical dosage form

EXAMPLE 28

75.76 parts by weight of the coprecipitate powder, obtained according to Example 1, are mixed with 24.05 parts by weight of HPMC-4000 CP and then mixed with 0.19 parts by weight of magnesium stearate and afterwards compressed to give tablets, each containing 90 mg of nimodipine. The tablets obtained are then coated.

EXAMPLE 29

74.12 parts by weight of the coprecipitate powder, obtained according to Example 1, are mixed with 21.74 parts by weight of HPMC-4000 CP, 3.95 parts by weight of HPMC-1500 CP and 0.19 part by weight of magnesium stearate and afterwards compressed to give tablets, each containing 90 mg of nimodipine. The tablets obtained are coated in analogy to Example 28.

EXAMPLE 30

67.15 parts by weight of the coprecipitate powder, obtained according to Example 18, are mixed with 32.6 parts by weight of HPMC 1500 CP and 0.25 part by weight of magnesium stearate and afterwards compressed to give tablets, each containing 90 mg of nimodipine. The tablets obtained are coated in analogy to Example 28.

EXAMPLE 31

84.2 parts by weight of the coprecipitate powder, obtained according to Example 2, are mixed with 15.6 parts by weight of HPMC-4000 CP, compacted in dry form, screened and then mixed with 0.2 part by weight of magnesium stearate and afterwards compressed to give tablets. The tablets obtained are then coated.

EXAMPLE 32

53.8 parts by weight of the coprecipitate powder, obtained according to Example 23, are mixed with 41 parts by weight of HPMC-4000 CP and 5 parts by weight of lactose and 0.2 part by weight of magnesium stearate and afterwards compressed to give tablets. The tablets obtained are then coated.

EXAMPLE 33

49.9 parts by weight of the coprecipitate powder, obtained according to Example 16, are mixed with the same amount of HPMC-15,000 CP and 0.2 part by weight of magnesium stearate and afterwards compressed to give tablets. The tablets obtained are then coated.

EXAMPLE 34

88 parts by weight of the coprecipitate powder, obtained according to Example 10, are mixed with 11.7 parts by weight of HPMC 100,000 CP and 0.3 part by weight of magnesium stearate and afterwards compressed to give tablets. The tablets obtained are then coated.

We claim:

1. Orally administrable solid pharmaceutical preparation for controlled release, comprising A) an active compound in amorphous form as coprecipitate in B) a polyvinylpyrrolidone homo or copolymer having a weight average molecular weight of about 15,000 to 1,000,000 and C) a release-delaying component consisting essentially of a gel-forming polymer having a viscosity of at least 15 mPas measured at a 2% concentration at 20° C. and, optionally, other auxiliaries and additives, wherein the active compound A), polyvinylpyrrolidone homo or copolymer B) and release-delaying component C) are present in a weight ratio relative to each other of A:B:C=1:0.5–10:0.01–15 said-preparation comprising crosslinked polymer.

2. Orally administrable solid pharmaceutical preparation according to claim 1, wherein the active compound is present in amorphous form as a coprecipitate with 1.0 to 4 parts by weight of polyvinylpyrrolidone having a weight-average molecular weight of about 15,000 to 100,000, per 1 part by weight of active compound.

3. Orally administrable solid pharmaceutical preparation according to claim 1, characterized in that, as release-delaying component, it contains 0.1 to 10 parts by weight of gel-forming cellulose ethers.

4. Orally administrable solid pharmaceutical preparation according to claim 1, characterized in that it contains active compounds which are dihydropyridines.

* * * * *

UNITED STATES PATENT AND TRADEMARK OFFICE
CERTIFICATE OF CORRECTION

PATENT NO. : 5,900,425
DATED : May 4, 1999
INVENTOR(S) : Venkata-Rangarao Kanikanti, et al.

It is certified that error appears in the above-indentified patent and that said Letters Patent is hereby corrected as shown below:

Col. 8, Line 4                      After "comprising" insert --no--

Signed and Sealed this

Sixteenth Day of November, 1999

Attest:

Q. TODD DICKINSON

*Attesting Officer*         *Acting Commissioner of Patents and Trademarks*